(12) United States Patent
Tracy et al.

(10) Patent No.: US 6,444,223 B1
(45) Date of Patent: Sep. 3, 2002

(54) METHOD OF PRODUCING SUBMICRON PARTICLES OF A LABILE AGENT AND USE THEREOF

(75) Inventors: Mark A. Tracy; Kevin L. Ward, both of Arlington; Warren E. Jaworowicz, Boxboro, all of MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 0 days.

(21) Appl. No.: 09/321,091

(22) Filed: May 28, 1999

(51) Int. Cl.[7] .......................... A61K 9/10; A61K 47/32; A61K 47/34
(52) U.S. Cl. ........................................ 424/486; 424/487
(58) Field of Search ................................ 424/486, 487, 424/497, 489; 514/951–952; 264/140; 451/28, 36

(56) References Cited

U.S. PATENT DOCUMENTS

| | | | |
|---|---|---|---|
| 5,019,400 A | 5/1991 | Gombotz et al. | 424/497 |
| 5,145,684 A | 9/1992 | Liversidge et al. | 424/489 |
| 5,307,640 A | 5/1994 | Fawzy et al. | 62/52.1 |
| 5,399,363 A | 3/1995 | Liversidge et al. | 424/490 |
| 5,475,984 A | 12/1995 | Fermani et al. | 62/64 |
| 5,518,187 A | 5/1996 | Bruno et al. | 241/5 |
| 5,534,270 A | 7/1996 | De Castro | 424/490 |
| 5,540,937 A | 7/1996 | Billot et al. | 424/489 |
| 5,591,456 A | 1/1997 | Franson et al. | 424/494 |
| 5,654,010 A | 8/1997 | Johnson et al. | 424/502 |
| 5,656,297 A | 8/1997 | Bernstein et al. | 424/484 |
| 5,667,808 A | 9/1997 | Johnson et al. | 424/501 |
| 5,674,534 A | 10/1997 | Zale et al. | 424/501 |
| 5,711,968 A | 1/1998 | Tracy et al. | 424/487 |
| 5,716,644 A | 2/1998 | Zale et al. | 424/497 |
| 5,817,343 A | 10/1998 | Burke | 424/489 |
| 5,912,015 A | 6/1999 | Bernstein et al. | 424/484 |
| 5,922,253 A | 7/1999 | Herbert et al. | 254/5 |

FOREIGN PATENT DOCUMENTS

| | | |
|---|---|---|
| EP | 0330180 A1 | 8/1989 |
| EP | 0499299 A2 | 8/1992 |
| WO | WO 90/13285 | 11/1990 |
| WO | WO 90/13780 | 11/1990 |
| WO | WO 95/29664 | 11/1995 |
| WO | WO 95/31973 | 11/1995 |
| WO | WO 97/42940 | 11/1997 |

OTHER PUBLICATIONS

Co–pending U.S. application No. 08/934,830 to Burke et al., "Device for the Sustained–Release of Aggregation–Stabilized, Biologically Active Agent," filed Sep. 22, 1997.

"Drug Nanocrystals for Improved Drug Delivery of Poorly Water Soluble Compunds," Presentation at CRS Meeting, Kyoto Japan Jul. 11, 1996, pp. 1–50 by G. Liversidge and E. Cooper.

Primary Examiner—Edward J. Webman
(74) Attorney, Agent, or Firm—Hamilton, Brook, Smith & Reynolds, P.C.

(57) ABSTRACT

The present invention relates to a sustained release composition comprising micron particles of labile agent and a method of preparing and using the sustained release composition. The invention further relates to micron particles of a labile agent and a method of preparing the micron particles. The method of the invention for preparing a composition for the sustained release of a labile agent, comprises forming a suspension comprising the labile agent dispersed in a polymer solution comprising at least one biocompatible polymer and at least one polymer solvent. The suspension is then wet milled to achieve micron particles of the labile agent. The polymer solvent is then removed resulting in a solid polymer/labile agent matrix. The method for preparing micron particles of a labile agent comprises forming a suspension comprising the labile agent, dispersed in a polymer solution comprising at least one biocompatible polymer and at least one polymer solvent, and wet milling of the suspension.

108 Claims, 3 Drawing Sheets

METHOD OF PRODUCING SUBMICRON PARTICLES OF A LABILE AGENT AND USE THEREOF

BACKGROUND OF THE INVENTION

It is known in the pharmaceutical industry that the rate of dissolution of a particulate drug can increase with increasing surface area (e.g., by decreasing particle size). This increase can result in enhanced bioavailability of the particulate drug. In sustained release compositions where a drug particle is dispersed within a matrix, for example, a polymer matrix, improvements in release profiles are typically seen as a result of a reduction in the particle size of the dispersed drug. Therefore, it is often desirable to minimize and control the particle size of a drug.

SUMMARY OF THE INVENTION

The present invention relates to a sustained release composition comprising micron partiles of a labile agent and a method of preparing and administering the sustained release composition. The invention further relates to micron particles of labile agent and a method of preparing the micron particles. The micron particles have a volume median particle size of less than about 2 microns. In a preferred embodiment, the particles arc submicron particles having a volume median particle size of less than 1 micron.

The method of the invention for preparing a composition for the sustained release of a labile agent, comprises the steps of:
  a) forming a suspension comprising the labile agent dispersed in a polymer solution comprising at least one biocompatible polymer and at least one polymer solvent;
  b) wet milling the suspension to achieve micron particles of the labile agent; and
  c) removing the polymer solvent thereby forming a solid polymer/labile agent matrix.

The method can further comprise the step of forming droplets of the milled suspension prior to removal of the polymer solvent. Further, the method can comprise freezing the droplets prior to removal of the polymer solvent. According to the method of the invention, the droplets can be microdroplets. In a specific embodiment wherein droplets are formed and then frozen, the polymer solvent can be removed by an evaporation and/or extraction process. In a preferred embodiment, the micron particles of labile agent are submicron in size.

The composition for sustained release of a labile agent is likewise prepared according to the method of the invention as described above. In other words, the composition for the sustained release of a labile agent as described herein is a composition prepared by the method comprising the steps of:
  a) forming a suspension comprising the labile agent dispersed in a polymer solution comprising at least one biocompatible polymer and at least one polymer solvent;
  b) wet milling the suspension to achieve micron particles of the labile agent; and
  c) removing the polymer solvent thereby forming a solid polymer/labile agent matrix.

The method for preparing micron particles of a labile agent comprises the step of (a) forming a suspension comprising the labile agent, dispersed in a polymer solution comprising at least one biocompatible polymer and at least one polymer solvent; and (b) wet milling the suspension. In a preferred embodiment, the particles of labile agent are submicron particles.

The micron particles of labile agent, as described herein, are prepared according to the method of the invention. Consequently, the micron particles of labile agent are prepared by forming a suspension comprising the labile agent, dispersed in a polymer solution comprising at least one biocompatible polymer and at least one polymer solvent, and wet milling the suspension.

The method described herein as compared to other known methods of particle size reduction, provides micron particles of proteins, peptides and oligonucleotides without agglomeration of the particles and with retention of biological activity. As shown in Example 1, known methods of particle size reduction such as sonication, are capable of achieving particles having a size of approximately 3 microns. However, achieving a particle size of about 2 microns or less without degradation of the labile agent can be readily achieved using the method described herein.

Importantly, the micron particles of labile agent once formed can, without isolation, be further processed to prepare a composition for the sustained release of labile agent. In addition, the sustained release compositions, which are prepared according to the claimed method, exhibit lower initial release of labile agent as a result of the micron particle size which they possess, thereby providing increased therapeutic benefits resulting from low peak serum concentrations and/or longer sustained duration.

DETAILED DESCRIPTION OF THE INVENTION

The features and other details of the composition and method of the invention, will now be more particularly described with references to the accompanying drawings and pointed out in the claims. It is understood that the particular embodiments of the invention are shown by way of illustration and not as limitations of the invention. The principle features of this invention can be employed in various embodiments without departing from the scope of the invention.

"Particle size" as that term is used herein refers to a volume median particle size as measured by conventional particle size measuring techniques well known to those skilled in the art, such as, laser diffraction, photon correlation spectroscopy, sedimentation field flow fractionation, disk centrifugation or electrical sensing zone. Laser diffraction is preferred.

As used herein, the term "micron particles" refers to particles having a volume median particle size of less than about 2 microns. In a preferred embodiment, the micron particles are submicron particles.

As used herein, the term "submicron particles" refers to particles having a volume median particle size of less than 1 micron. The volume median particle size is the median diameter of the volume-weighted size distribution.

The method of the invention for preparing a composition for the sustained release of a labile agent, comprises the steps of:

a) forming a suspension comprising the labile agent dispersed in a polymer solution comprising at least one biocompatible polymer and at least one polymer solvent;

b) wet milling the suspension to achieve micron particles of the labile agent; and c) removing the polymer solvent thereby forming a solid polymer/labile agent matrix.

The method can further comprise the step of forming droplets of the milled suspension prior to removal of the polymer solvent. Further, the method can comprise freezing the droplets prior to removal of the polymer solvent. According to the method of the invention, the droplets can be microdroplets. In a specific embodiment wherein droplets are formed and then frozen, the polymer solvent can be removed by an evaporation and/or extraction process. In a preferred embodiment, the micron particles are submicron in size.

The composition for sustained release of a labile agent is likewise prepared according to the method of the invention. In other words, the composition for the sustained release of a labile agent as described herein is a composition prepared by the method comprising the steps of:

a) forming a suspension comprising the labile agent dispersed in a polymer solution comprising at least one biocompatible polymer and at least one polymer solvent;

b) wet milling the suspension to achieve micron particles of the labile agent; and c) removing the polymer solvent thereby forming a solid polymer/labile agent matrix.

The method for preparing micron particles of a labile agent comprises the step of (a) forming a suspension comprising the labile agent, dispersed in a polymer solution comprising at least one biocompatible polymer and at least one polymer solvent; and (b) wet milling the suspension.

The micron particles of labile agent, as described herein, are prepared according to the method of the invention. Consequently, the micron particles of labile agent are prepared by forming a suspension comprising the labile agent, dispersed in a polymer solution comprising at least one biocompatible polymer and at least one polymer solvent, and wet milling the suspension.

A "labile agent" as that term is used herein, is a protein, polypeptide or oligonucleotide, or the pharmaceutically acceptable salt thereof, which is in its molecular, biologically active form when released in vivo, thereby possessing the desired therapeutic, prophylactic and/or diagnostic properties in vivo. Suitable proteins include, but are not limited to, immunoglobulins, antibodies, cytokines (e.g., lymphokines, monokines, chemokines), interleukins, interferons, erythropoietin, nucleases, tumor necrosis factor, colony stimulating factors, insulin, enzymes (e.g., superoxide dismutase, a plasminogen activator), tumor suppressors, blood proteins, hormones and hormone analogs (e.g., a growth hormone such as, human growth hormone (hGH), adrenocorticotropic hormone, leutinizing hormone releasing hormone (LHRH)), vaccines (e.g., tumoral, bacterial and viral antigens), antigens, growth factors and blood coagulation factors. Suitable polypeptides include protein inhibitors, protein antagonists, and protein agonists. Examples of oligonucleotides suitable for use in the invention include, but are not limited to, antisense molecules, ribozymes, antisense oligonucleotides, peptide nucleic acids, decoy RNAs and "dumbbell" DNAs also known as transcription factor decoy DNAs.

In one embodiment, the labile agent is stabilized. The labile agent can be stabilized against degradation, loss of potency and/or loss of biological activity, all of which can occur during formation of the micron particles, during formation of the sustained release composition having the micron particles dispersed therein, and/or prior to and during in vivo release of the labile agent. In one embodiment, stabilization can result in a decrease in the solubility of the labile agent, the consequence of which is a reduction in the initial release of labile agent, in particular, when release is from a sustained release composition. In addition, the period of release of the labile agent can be prolonged.

Stabilization of the labile agent can be accomplished, for example, by the use of a stabilizing agent. "Stabilizing agent", as that term is used herein, is any agent which binds or interacts in a covalent or non-covalent manner or is included with the labile agent. Stabilizing agents suitable for use in the invention are described in co-pending U.S. patent application Ser. No. 08/934,830 to Burke et al., filed on Sep. 22, 1997 and U.S. Pat. No. 5,711,968 to Tracy et al., U.S. Pat. No. 5,654,010 and U.S. Pat. No. 5,667,808 to Johnson et al., and U.S. Pat. No. 5,716,644 and U.S. Pat. No. 5,674,534 to Zale et al., the entire teachings of which are incorporated herein by reference. For example, a metal cation can be complexed with the labile agent, or the labile agent can be complexed with a polycationic complexing agent such as protamine, albumin, spermidine and spermine, or associated with a "salting-out" salt.

Suitable metal cations include any metal cation capable of complexing with the labile agent. A metal cation-stabilized labile agent, as defined herein, comprises a labile agent and at least one type of metal cation wherein the cation is not significantly oxidizing to the labile agent. In a particular embodiment, the metal cation is multivalent, for example, having a valency of +2 or more. It is preferred that the metal cation be complexed to the labile agent.

Suitable stabilizing metal cations include biocompatible metal cations. A metal cation is biocompatible if the cation is non-toxic to the recipient, in the quantities used, and also presents no significant deleterious or untoward effects on the recipient's body, such as a significant immunological reaction at the injection site. The suitability of metal cations for stabilizing labile agents and the ratio of metal cation to labile agent needed can be determined by one of ordinary skill in the art by performing a variety of stability indicating techniques such as polyacrylamide gel electrophoresis, isoelectric focusing, and HPLC analyses (e.g., Size Exclusion, Reversed Phase and other Ion Exchange) on particles of metal cation-stabilized labile agents prior to and following particle size reduction and/or encapsulation. The molar ratio of metal cation to labile agent is typically between about 1:2 and about 100:1, preferably between about 2:1 and about 10.1.

Examples of stabilizing metal cations include, but are not limited to, $K^+$, $Zn^{+2}$, $Mg^{+2}$ and $Ca^{+2}$. Stabilizing metal cations also include cations of transition metals, such as $Cu^2$. Combinations of metal cations can also be employed. In a particular embodiment, $Zn^{+2}$ is used as a stabilizing metal cation for hGH at a zinc cation component to hGH molar ratio of about 4:1 to about 100:1. In a preferred embodiment, the zinc cation component to hGH molar ratio is about 4:1 to about 10:1, and most preferably 10:1.

The labile agent can also be stabilized with at least one polycationic complexing agent. Suitable polycationic complexing agents include, but are not limited to, protamine, and albumin. The suitability of polycationic complexing agents for stabilizing labile agents can be determined by one of ordinary skill in the art in the manner described above for stabilization with a metal cation. An equal weight ratio of polycationic complexing agent to labile agent is suitable.

The suspension which is milled comprises a labile agent dispersed in a polymer solution. The concentration of the labile agent in the suspension can be in the range from between about 0.01% to about 50% w/w, preferably from between about 0.1% to about 30% (w/w) of the combined weight of the polymer and labile agent.

The use of a polymer solution allows particle size reduction of the labile agent to occur without significant degradation and aggregation of the labile agent. The polymer solution comprises a biocompatible polymer which is solubilized in a suitable polymer solvent at a concentration which results in achieving milling of the labile agent without aggregation or degradation of said agent. A suitable concentration for the polymer solution can range between about 0.1% w/v to about 100% w/v, more preferably between about 1% w/v to about 30% w/v. The concentration of the polymer needed to achieve the desired micron particles of labile agent can be determined as described herein. The polymer solution can comprise one or more solvents.

A suitable polymer solvent is a solvent in which the polymer is soluble but in which the labile agent is substantially insoluble and non-reactive resulting in suspension of the labile agent in the polymer solution. Examples of suitable polymer solvents include organic liquids, such as methylene chloride, chloroform, ethyl acetate, dimethylsulfoxide, methyl acetate, hexafluoroisopropanol, acetone and combinations thereof.

A polymer is biocompatible if the polymer and any degradation products of the polymer are non-toxic to the recipient and also possess no significant deleterious or untoward effects on the recipient's body, such as a significant chronic immunological reaction at the injection site.

"Biodegradable", as defined herein, means the composition will degrade or erode in vivo to form smaller chemical species. Degradation can result, for example, by enzymatic, chemical and/or physical processes. Suitable biocompatible, biodegradable polymers include, for example, poly(lactide)s, poly(glycolide)s, poly(lactide-co-glycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polyacetals, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends or copolymers thereof.

Biocompatible, non-biodegradable polymers suitable for use in the invention, include, for example, polyacrylates, polymers of ethylene-vinyl acetates and acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

Further, the terminal functionalities or pendant groups of the polymers can be modified, for example, to modify hydrophobicity, hydrophilicity and/or provide, remove or block moieties which can interact with the active agent (via, for example ionic or hydrogen bonding).

Acceptable molecular weights for polymers used in this invention can be determined by a person of ordinary skill in the art taking into consideration factors such as the desired polymer degradation rate, physical properties such as mechanical strength, and rate of dissolution of polymer in solvent and viscosity. Typically, an acceptable range of molecular weight is about 2,000 Daltons to about 2,000,000 Daltons. In a preferred embodiment, the polymer is a biodegradable polymer or copolymer. In a more preferred embodiment, the polymer is poly(lactide-co-glycolide) (herein after "PLG") with a lactide:glycolide ratio of about 1:1 and a molecular weight of about 5,000 Daltons to about 70,000 Daltons. In an even more preferred embodiment, the molecular weight of the PLG used in the present invention has a molecular weight of about 5,000 Daltons to about 42,000 Daltons.

Wet milling of the suspension comprising the labile agent dispersed in a polymer solution can be accomplished by adding a grinding media to the suspension and applying a mechanical means to reduce the particle size of the labile agent to a volume median particle size of about 2 microns or less, preferably less than about 1 micron (submicron). The mechanical means applied to reduce the particle size, can take the form of a dispersion mill or any blender. Suitable dispersion mills include a rotary mill, a ball mill, an attrition mill, a vibratory mill, a planetary mill, media mills such as a sand mill, and a bead mill. A rotary blender such as the Shaker Mixer, TURBULA® Type T2C, available from Glen Mills of Clifton N.J.) is preferred. When using the TURBULA® Shaker Mixer, the particle size of the sample is reduced by rotating a container having the sample and grinding media disposed therein.

The grinding media can be selected from rigid media preferably spherical or particulate in form having an average size less than about 5 mm, preferably less than about 3 mm. In selecting a material for use as a grinding media the material should be harder than the labile agent and stable in the milling medium to achieve successful milling. Examples of media suitable for use in the invention include zirconium silicate, zirconium oxide, such as 95% ZrO stabilized with magnesia, glass, stainless steel, titania, alumina, and 95% ZrO stabilized with yttrium.

The milling time can vary and can depend upon, for example, the composition of the suspension being milled, the grinding media employed, and the mechanical means being applied. For example, the particle size of the labile agent at the commencement of milling is an important factor in the length of time needed to achieve micron particles of labile agent. Advantageously, the particle size of the suspension can be determined at any time during the milling process by removing a sample of the suspension and performing particle size analysis using the techniques described above. Typically, the suspension is milled for between about 24 and about 72 hours.

Milling of the suspension should be conducted at a temperature which does not significantly degrade the labile agent. As such, a suitable milling temperature can be determined based on the labile agent present. Typically, the milling temperature will be less than about 30° C. In a preferred embodiment, milling is conducted at about 10° C. In a more preferred embodiment milling is conducted at about 4° C.

The term "sustained release composition" as defined herein, comprises a polymer and micron particles of a labile agent (also referred to herein as a "polymer/labile agent matrix"). The polymers of the invention are biocompatible. Suitable biocompatible polymers, can be either biodegradable or non-biodegradable polymers or blends or copolymers thereof, as described herein.

The sustained release compositions of this invention can be formed into many shapes such as a film, a pellet, a cylinder, a disc or a microparticle. A "microparticle" as defined herein, comprises a polymer component having a diameter of less than about one millimeter and having micron particles of labile agent dispersed therein. A microparticle can have a spherical, non-spherical or irregular shape. Typically, the microparticle will be of a size suitable for injection. A preferred size range for microparticles is from about one to about 180 microns in diameter.

As defined herein, a sustained release of labile agent is release of the labile agent from a biocompatible polymer matrix which occurs over a period which is longer than that period during which a biologically significant amount of the labile agent, would be available following direct administration of a solution of the labile agent. It is preferred that a sustained release be a release of labile agent which occurs over a period of greater than two days. A sustained release of labile agent, from a polymer matrix can be a continuous or a discontinuous release, with relatively constant or varying rates of release. The continuity of release and level of release can be affected by the type of polymer composition used (e.g., monomer ratios, molecular weight, and varying combinations of polymers), labile agent loading, and/or selection of excipients to produce the desired effect.

The amount of stabilized labile agent, which is contained within the polymer/labile agent matrix of a sustained release composition, is a therapeutically effective amount which can be determined by a person of ordinary skill in the art, taking into consideration factors such as body weight, condition to be treated, type of polymer used, and release rate from the polymer. A "therapeutically effective amount", as used herein, is the amount of the composition for the sustained release of a labile agent from a polymer matrix, necessary to elicit the desired biological response following administration.

Typically, the sustained release composition can contain from about 0.01% (w/w) to about 50% (w/w) of labile agent (dry weight of composition). The amount of agent used will vary depending upon the desired effect of the agent, the planned release levels, and the time span over which the agent will be released. A preferred range of agent loading is between about 0.1% (w/w) to about 30% (w/w) agent. A more preferred range of agent loading is between about 0.5% (w/w) to about 20% (w/w) agent.

In another embodiment, the sustained release composition can contain excipients. The excipients can be added to the suspension prior to or following milling. These excipients are added to maintain the potency of the labile agent over the duration of release and modify polymer degradation. Suitable excipients include, for example, carbohydrates, amino acids, fatty acids, surfactants, and bulking agents, and are known to those skilled in the art. The amount of excipient used is based on ratio to the labile agent, on a weight basis. For amino acids, fatty acids and carbohydrates, such as sucrose, lactose, mannitol, dextran and heparin, the ratio of carbohydrate to labile agent, is typically between about 1:10 and about 20:1. For surfactants, such as TWEEN™ and PLURONIC™, the ratio of surfactant to labile agent is typically between about 1:1000 and about 1:20.

Bulking agents typically comprise inert materials. Suitable bulking agents are known to those skilled in the art.

The excipient can also be a metal cation component which is separately dispersed within the polymer matrix. This metal cation component acts to modulate the release of the labile agent, by for example, modifying polymer degradation and is not complexed with the labile agent. The metal cation component can optionally contain the same species of metal cation, as is contained in the metal cation stabilized labile agent, and/or can contain one or more different species of metal cation. The metal cation component acts to modulate the release of the labile agent from the polymer matrix of the sustained release composition and can enhance the stability of the labile agent in the composition. A metal cation component used in modulating release typically comprises at least one type of multivalent metal cation. Examples of metal cation components suitable to modulate release include or contain, for example, $Mg(OH)_2$, $MgCO_3$ (such as $4MgCO_3.Mg(OH)_2.5H_2O$), $MgSO_4$, $Zn(OAc)_2$, $Mg(OAc)_2$, $ZnCO_3$ (such as $3Zn(OH)_2.2ZnCO_3$), $ZnSO_4$, $ZnCl_2$, $MgCl_2$, $CaCO_3$, zinc citrate and magnesium citrate. A suitable ratio of metal cation component to polymer is between about 1:99 to about 1:2 by weight. The optimum ratio depends upon the polymer and the metal cation component utilized. A polymer matrix containing a dispersed metal cation component to modulate the release of a biologically active agent from the polymer matrix is further described in U.S. Pat. No. 5,656,297 to Bernstein et aL and co-pending U.S. patent application Ser. No. 09/056,566 filed on Apr. 7, 1998, the teachings of both of which are incorporated herein by reference in their entirety.

In yet another embodiment, at least one pore forming agent, such as a water soluble salt, sugar or amino acid, is included in the sustained release composition to modify the microstructure. The proportion of pore forming agent added to the suspension comprising micron particles of labile agent dispersed in a solution comprising at least one biocompatible polymer and at least one polymer solvent, is between about 1% (w/w) to about 30% (w/w). It is preferred that at least one pore forming agent be included in a nonbiodegradable polymer matrix of the present invention.

Suitable methods for forming a composition for the sustained release of labile agent are described in U.S. Pat. No. 5,019,400, issued to Gombotz et al., and co-pending U.S. patent application Ser. No. 08/443,726, filed May 18, 1995, the teachings of which are incorporated herein by reference in their entirety. This method of formation, as compared with other methods such as phase separation, can also reduce the amount of labile agent required to produce a sustained release composition with a specific labile agent content.

In this method, a suspension comprising micron particles of the labile agent dispersed in a solution comprising at least one biocompatible polymer and at least one polymer solvent is processed to create droplets, wherein at least a significant portion of the droplets contains polymer, polymer solvent and the micron particles of labile agent. These droplets are then frozen by a suitable means. Examples of means for processing the suspension to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/labile agent matrix comprising a biocompatible polymer and micron particles of a labile agent. Mixing ethanol with other non-solvents, such as hexane, heptane or pentane, can increase the rate of solvent extraction, above that achieved by ethanol alone, from certain polymers, such as poly (lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

Yet another method of forming a sustained release composition, from a suspension comprising a biocompatible polymer and micron particles of a labile agent, includes film casting, such as in a mold, to form a film or a shape. For instance, after putting the suspension into a mold, the polymer solvent is then removed by means known in the art, or the temperature of the polymer suspension is reduced, until a film or shape, with a consistent dry weight, is obtained. Film casting of a polymer solution, is further described in U.S. Pat. No. 5,656,297, the teachings of which are incorporated herein by reference in their entirety.

Without being bound by a particular theory it is believed that the release of the labile agent can occur by two different mechanisms. First, the labile agent can be released by diffusion through aqueous filled channels generated in the polymer matrix, such as by the dissolution of the labile agent, or by voids created by the removal of the polymer solvent during the preparation of the sustained release composition. A second mechanism is the release of the labile agent, due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer. Hydrophilic excipients such as salts, carbohydrates, and surfactants can also be incorporated to increase hydration which can alter the rate of erosion of the polymer.

By altering the properties of the polymer, the contributions of diffusion and/or polymer degradation to labile agent release can be controlled. For example, increasing the glycolide content of a poly(lactide-co-glycolide) polymer and decreasing the molecular weight of the polymer can enhance the hydrolysis of the polymer, and thus provides an increased labile agent release from polymer erosion.

In addition, the rate of polymer hydrolysis is increased in non-neutral pH. Therefore, an acidic or a basic excipient can be added to the polymer suspension, used to form the sustained release composition, for example, microparticles, to alter the polymer erosion rate.

The composition of this invention can be administered to a human, or other animal, by injection, implantation (e.g., subcutaneously, intramuscularly, intraperitoneally, intracranially, and intradermally), administration to mucosal membranes (e.g., intranasally, intravaginally, intrapulmonary or by means of a suppository), or in situ delivery (e.g., by enema or aerosol spray) to provide the desired dosage of labile agent based on the known parameters for treatment with the particular agent of the various medical conditions.

EXEMPLIFICATIONS

POLYMER

The polymers employed in the following examples are described below:

RG 502H: 50:50 poly(D,L-lactide-co-glycolide) (PLG) with hydrophilic end groups, nominal MW 10 k Daltons purchased from Boehringer Ingelheim Chemicals, Inc. of Montvale, N.J.

MEDISORB® 5050 2A: 50:50 poly(D,L-lactide-co-glycolide) (PLG) with hydrophilic end groups, nominal MW 8 k Daltons, purchased from Alkermes, Inc. of Cincinnati, Ohio.

GENERAL PROCESS FOR THE PREPARATION OF POLYMER MICROPARTICLES

Forming droplets of the milled suspension by atomizing the milled suspension comprising submicron particles of at least one labile agent dispersed in a solution of at least one biocompatible polymer, at least one polymer solvent and any excipients.

Freezing the droplets by contact with liquid nitrogen.

Extracting the polymer solvent from the frozen droplets into an extraction solvent (e.g., –80° C. ethanol), thereby forming microparticles comprising a polymer/labile agent matrix.

Isolating the microparticles from the extraction solvent by filtration.

Removing any remaining solvent from the microparticles.

Sizing of the microparticles by passage through an appropriately sized mesh.

EXAMPLE 1

PREPARATION OF SUBMICRON PARTICLES OF ZINC-COMPLEXED hGH

STEP A. FORMATION OF $Zn^{+2}$:hGH PROTEIN COMPLEX

Bulk hGH whose DNA sequence is described in U.S. Pat. No. 4,898,830, issued to Goeddel et al. was provided at 20 mg/mL in 25 mM sodium bicarbonate. It was complexed with 54.5 mM zinc acetate at a 10:1 zinc to hGH ratio.

The suspension of $Zn^{+2}$-complexed hGH was atomized using an ultrasonic nozzle (Type ViA: Sonics and Material, Danbury, Conn.) and sprayed into a polypropylene tub containing liquid nitrogen to form frozen particles. The polypropylene tub was then placed into a –80° C. freezer until the liquid nitrogen evaporated. The frozen particles, which contained $Zn^{+2}$-complexed hGH, were then lyophilized to yield dry Zn:hGH powder.

STEP B. MILLING OF PARTICLES 400 mg of zinc-complexed hGH, prepared according to Step A, was suspended in 15 mL of a 10% solution of PLG (RG 502H) in methylene chloride. The suspension was milled at approximately 4° C. using a rotary blender (TURBULA® Model T2C available from Glen Mills of Clifton, N.J.) and 10 g of 100 μm zirconia silicate beads. Milling time was approximately 48 hours.

Particle size analysis was conducted on the suspension upon the completion of milling using a Coulter LS 130 laser diffraction instrument with small volume nodule. The particles of the milled suspension had a volume median particle size of 0.2 microns. Particle size analysis was also conducted on a sample of the $Zn^{+2}$-complexed hGH prior to milling, and on a sample of $Zn^{+2}$-complexed hGH which had been sonicated for approximately four minutes with a tapered microtip in an ice bath, as an alternative method of particle size reduction. Results showed that the unprocessed complex had a volume median particle size of 16.2 μm and the sonicated complex had a volume median particle size of 3 μm.

EXAMPLE 2

ENCAPSULATION AND IN VITRO RELEASE OF hGH

Two separate formulations of microparticles containing the milled and sonicated $Zn^{+2}$-complexed hGH particles described in Step B of Example 1, were prepared using the "General Process" described above. In each case, the differently sized particles were present in their respective solutions (10% RG 5 02H in methylene chloride) at an amount necessary to achieve a theoretical load of 16% in the final microparticle. $ZnCO_3$, sufficient for a 1% load in the final microparticle, was also present at the onset of the "General Process."

The two microparticle formulations formed as described above, and having milled and sonicated $Zn^{+2}$-complexed hGH incorporated therein, were evaluated for their in vitro release of drug over the first 24 hours. The hGH-containing microparticles were hydrated in buffer (150 mM phosphate with 0.1% Pluronic™ F68 at pH 7.3) at 4° C. A sample of buffer was removed following the first 24 hours of incubation. Released protein was quantified by BioRad Protein Assay (BioRad, Inc., Richmond, Calif.). The initial release of hGH from the microparticles containing the sonicated protein (volume median particle size 3.3 μm) over the first 24 hours was approximately 48%. The initial release of hGH from the microparticles containing the milled protein (volume median particle size 0.2 μm) over the first 24 hours was 6%.

The results show that hGH-containing microparticles, wherein the particle size of the incorporated hGH is in the submicron range, exhibit a reduction in the initial release of protein when compared to hGH-containing microparticles wherein the particle size of the incorporated protein has a volume median particle size of 3.3 microns.

EXAMPLE 3

Five solutions, each containing 250 mgs of $Zn^{+2}$-complexed hGH prepared according to Example 1, 1 g of MEDISORB® 5050 2A polymer, and 17 mL of methylene chloride were prepared. All solutions were sonicated for four minutes prior to milling using a microtip probe available from Sonics and Material, Danbury Conn. 10 gms of zirconium silicate beads (100 μm diameter) were added to each solution. Four of the solutions were wet milled for 4.5, 22, 48, and 72 hours, and are identified as solutions 2–5, respectively of Table 1. Solution 1 was not subjected to the milling process. Milling was conducted at a temperature of about 4° C., using a TURBULA® blender Model T2C. at a speed of approximately 96 r.p.m.

At each end point, a sample of solution was removed and subjected to particle size analysis using a Coulter LS 130. The volume median particle size of solutions 1–5 is presented in Table 1.

TABLE 1

| Solution Identification | Milling Time (Hours) | Volume Median Particle Size of $Zn^{+2}$-complexed hGh (Microns) |
|---|---|---|
| 1 | 0 | 3.619 |
| 2 | 4.5 | 1.244 |
| 3 | 22 | 0.590 |
| 4 | 48 | 0.436 |
| 5 | 72 | 0.416 |

EXAMPLE 4

ENCAPSULATION AND IN VITRO RELEASE OF hGH

PART A: MICROPARTICLE FORMATION

Microparticles containing the $Zn^{+2}$-complexed hGH particles of Solutions 1–5 of Example 4 and 1% $ZnCO_3$ were prepared using the "General Process" described above. A description of each microparticle formulation prepared is presented in Table 2. The number designation of the formulations in Table 2 reflects encapsulation of the solution having the same number designation as in Table 1 of Example 3.

PART B: IN VITRO RELEASE

Microparticle Formulations 1–5 were evaluated for their in vitro release of drug over the first 24 hours. Duplicate microparticle formulations were hydrated in buffer (50 mM HEPES, 10 mM KCl, 0.1% $NaN_3$) at 37° C. The amount of protein released at 24 hours post hydration was quantified using the BioRad Protein Assay (BioRad, Inc. Richmond, Calif.). The results of the assay are presented in Table 2.

TABLE 2

| Micro-Particle Formulation Identification | Amount of Micro-Particles Assayed (mgs) | Actual hGH Load (% w/w) | Amount of hGH in Micro-Particles (μgs) | % hGH Released Over First 24 Hours | Average (SD) |
|---|---|---|---|---|---|
| 1 | 9.5 | 17.4 | 1653 | 28 | 29.3 |
|   | 8.3 | 17.4 | 1444.2 | 30 | (1.3%) |
| 2 | 8.2 | 16.8 | 1377.6 | 15 | 15.4 |
|   | 8.0 | 16.8 | 1344 | 15 | (0.2%) |
| 3 | 9.5 | 16.9 | 1605.5 | 8 | 8.3 |
|   | 8.8 | 16.9 | 1487.2 | 9 | (0.4%) |
| 4 | 9.1 | 16.8 | 1528.8 | 5 | 4.8 |
|   | 8.8 | 16.8 | 1478.4 | 5 | (0.3%) |
| 5 | 9.3 | 16.7 | 1553.1 | 4 | 4.0 |
|   | 9.8 | 16.7 | 1636.6 | 4 | (0.4%) |

Figure 1:
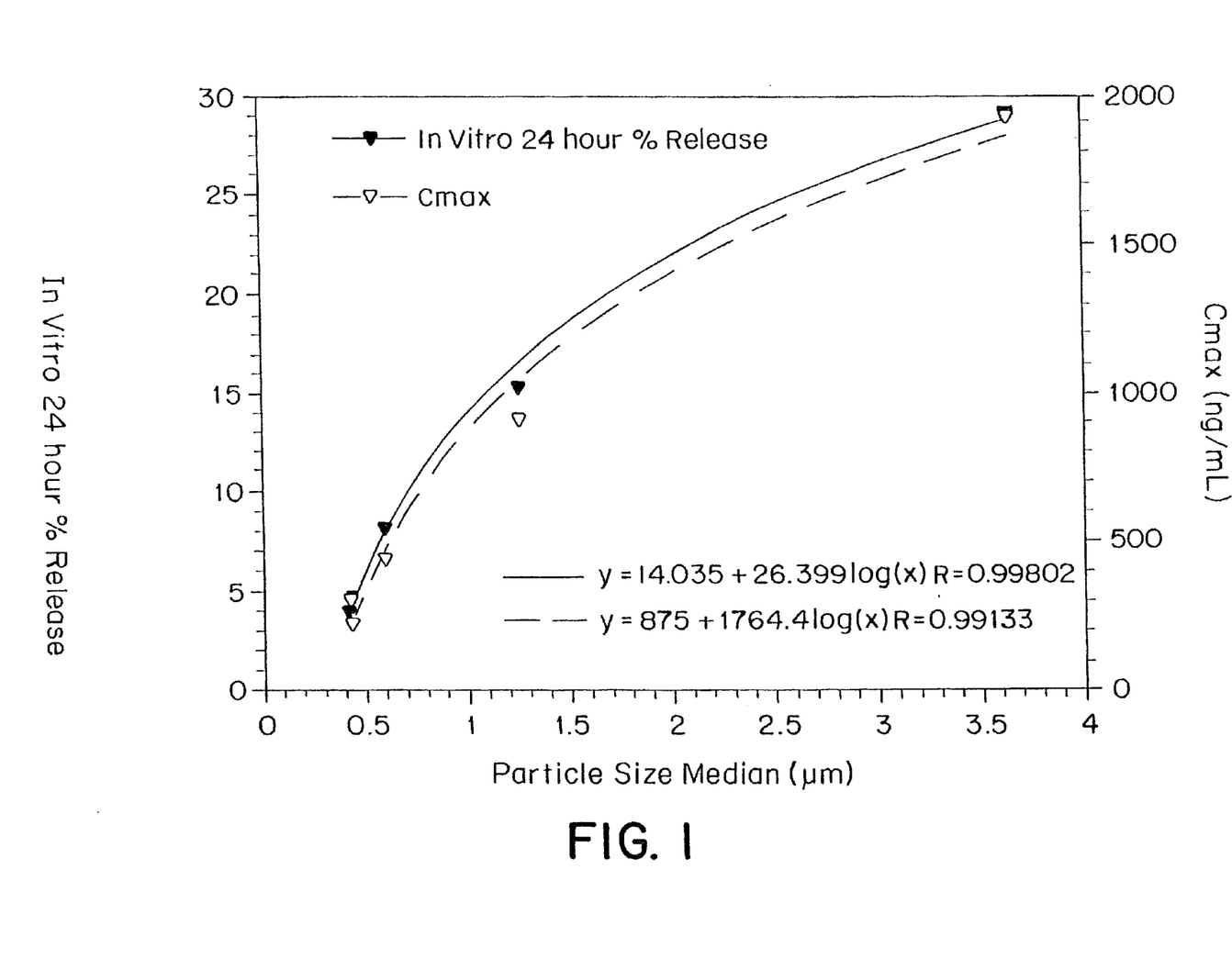
FIG. 1 is a graph showing the % release in vitro (% of theoretical load) and the $C_{max}$ in vivo of human growth hormone (hGH) over the first twenty-four hours from the hGH-containing microparticles of Example 4, as a function of the particle size of the $Zn^{+2}$-complexed hGH prior to encapsulation. Doses were normalized based on the weight of the test animal.

The in vitro release as determined above for Formulations 1–5 is plotted as a function of the volume median particle size in FIG. 1. The results show that release over the first 24 hours is directly related to the volume median particle size of the protein prior to encapsulation.

EXAMPLE 5

IN VIVO RELEASE OF hGH

Studies were conducted in rats to determine the in vivo release rate of hGH from Microparticle Formulations 1–5 of Example 4 over the first 24 hours following treatment. Male Sprague-Dawley rats were injected subcutaneously with a dose of approximately 15 mg/kg of hGH. The amount of Formulations 1–5 needed to achieve this dose was based on the % theoretical load of the formulations. The microparticles were suspended in 0.75 mL of an aqueous injection vehicle comprising 3% CMC (low viscosity), 0.1% polysorbate 20, in 0.9% NaCl.

Blood samples were collected at the following intervals: 0.08, 0.17, 0.25, 0.42 and 1.00 days. The blood samples were clotted and hGH concentrations in serum were determined using an ELISA provided in a rhGH kit available from Boehringer Mannheim (Catalog No.: 15868). The results are presented in Table 3 as an average of the three test animals in each treatment group.

TABLE 3

| Microparticle Formulation | Time-point (Days) | Average Concentration of hGH in Serum (ng/mL) |
| --- | --- | --- |
| 1 | 0.08 | 1933.67 |
|   | 0.17 | 1642.33 |
|   | 0.25 | 1701.00 |
|   | 0.42 | 1275.00 |
|   | 1.00 | 41.87 |
| 2 | 0.08 | 838.33 |
|   | 0.17 | 690.00 |
|   | 0.25 | 907.33 |
|   | 0.42 | 460.33 |
|   | 1.00 | 62.40 |
| 3 | 0.08 | 392.00 |
|   | 0.17 | 405.67 |
|   | 0.25 | 442.50 |
|   | 0.42 | 274.67 |
|   | 1.00 | 24.23 |
| 4 | 0.08 | 228.00 |
|   | 0.17 | 229.33 |
|   | 0.25 | 216.40 |
|   | 0.42 | 148.00 |
|   | 1.00 | 40.40 |
| 5 | 0.08 | 211.67 |
|   | 0.17 | 269.33 |
|   | 0.25 | 302.50 |
|   | 0.42 | 171.45 |
|   | 1.00 | 18.37 |

Figure 2:
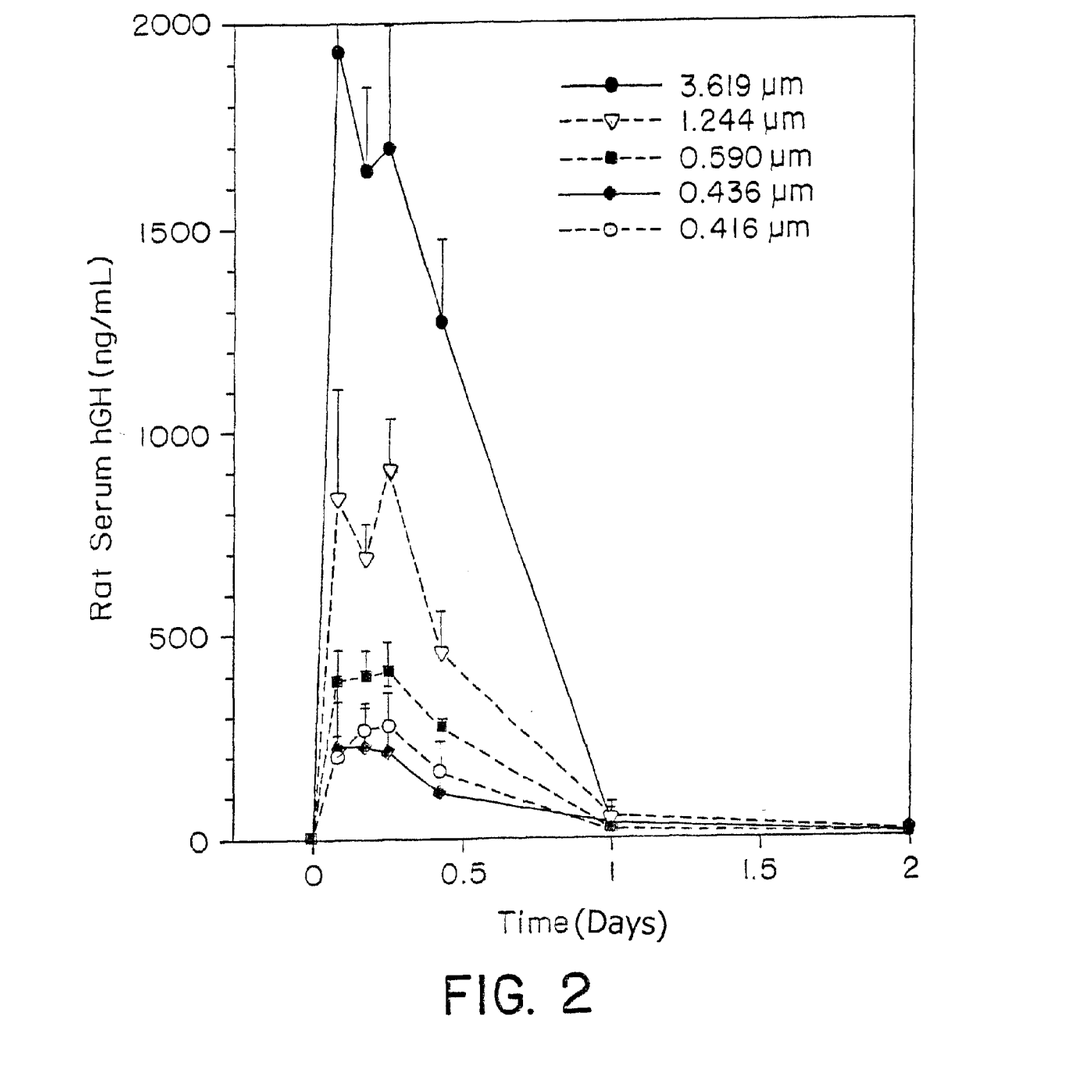
FIG. 2 is a plot of the amount of hGH in serum (ng/mL) at predetermined intervals over the first 48 hours following administration of the hGH-containing microparticles of Example 4 versus time (Days).

The results presented in Table 3 demonstrate that the in vivo release from Microparticle Formulations 1–5 over the first 24 hours following administration, decreases as the particle size of the $Zn^{+2}$-complexed hGH decreases. These results are presented graphically in FIG. 2. The average Cmax (ng/mL) for each treatment group over the first 24 hour period following administration is plotted as a function of particle size of the $Zn^{+2}$-complexed hGH prior to encapsulation in FIG. 1. The plot shows that $C_{max}$ is directly related to the size of the $Zn^{+2}$-complexed hGH prior to encapsulation.

EXAMPLE 6

IN VIVO RELEASE OF hGH

Microparticles containing 16% hGH, 1% $ZnCO_3$ and MEDISORB® 5050 2A polymer were prepared according to the procedures outlined above for the preparation of Microparticle Formulation 5. The volume median particle size of the $Zn^{+2}$-complexed hGH prior to encapsulation was determined to be 0.5 microns.

The release of hGH from microparticles having the 0.5 micron labile agent incorporated therein and Microparticle Formulation 1 (Control) were evaluated in vivo according to the method described in Example 5, but over a 24 day period.

Figure 3:
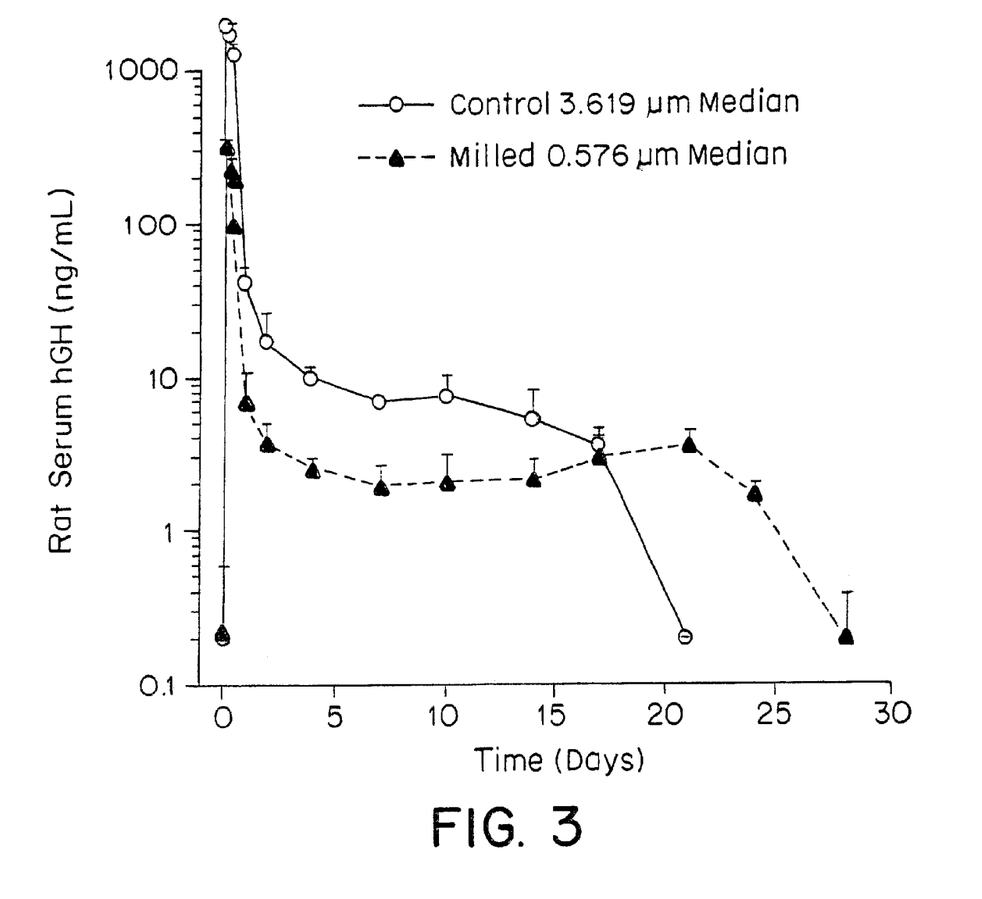
FIG. 3 is a plot of the amount of hGH in serum (ng/mL) at predetermined intervals over a 24 day period following administration of hGH-containing microparticle formulations described herein versus time (Days).

The hGH concentration in serum (ng/mL) was plotted as a function of time in FIG. 3. The plot shows a decrease in the $C_{max}$ and a longer period of sustained release for the microparticles having $Zn^{+2}$-complexed hGH with a particle size of 0.5 microns as compared to the control.

EXAMPLE 7

WET MILLING WITH PLURONIC™ F68 AND/ OR PLG

Particles of $Zn^{+2}$-complexed hGH were prepared using a 10:1 molar ratio of zinc component to hGH according to the method of Example 1. The $Zn^{+2}$-complexed hGH was separately suspended in each of the following solutions to achieve a final concentration of 22 mg/mL of hGH in methylene chloride:

A—1% solution of F68 in methylene chloride.

B—10% solution of poly(lactic-co-glycolic acid) (PLG RG502H) in methylene chloride; and C—10% solution of poly(lactic-co-glycolic acid) (PLG RG502H) in methylene chloride with 1% F68.

Suspensions A, B and C. were wet milled for 48 hours at a temperature of approximately 4° C. Particle size analysis was performed using a Coulter LS130. The results are presented below.

Suspension A: Approximately 48% of the total volume was made up of particles smaller than a micron, with the remainder made up of particles between 1 and 10 $\mu$. The volume median particle size in this case was 1.2 $\mu$.

Suspensions B and C: Approximately 95% of the total volume consisted of particles smaller than 1 $\mu$m, with a volume median particle size of 210 nm.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method for preparing a composition for the sustained release of a labile agent, comprising the steps of:

a) forming a suspension comprising human growth hormone complexed to a stabilizing metal cation and dispersed in a polymer solution comprising at least one biocompatible polymer and at least one polymer solvent;

b) wet milling the suspension to achieve submicron particles of the labile agent; and c) removing the polymer solvent thereby forming a solid polymer matrix having the labile agent dispersed therein.

2. The method of claim 1 wherein the human growth hormone is complexed to $Zn^{+2}$.

3. A method for preparing a composition for the sustained release of a labile agent, comprising the steps of:

a) forming a suspension comprising the labile agent wherein the labile agent is a protein, polypeptide or oligonucleotide dispersed in a polymer solution comprising a poly(lactide-co-glycolide) polymer and at least one polymer solvent;

b) wet milling the suspension to achieve submicron particles of the labile agent; and c) removing the polymer solvent thereby forming a solid polymer matrix having the labile agent dispersed therein.

4. A method for preparing a composition for the sustained release of a labile agent, comprising the steps of:

a) forming a suspension comprising the labile agent wherein the labile agent is a protein, polypeptide or oligonucleotide dispersed in a polymer solution comprising at least one biocompatible polymer and a polymer solvent selected from the group consisting of methylene chloride, chloroform, acetone, ethyl acetate, methyl acetate, dimethylsulfoxide, hexafluoroisopropanol and any combinations thereof;

b) wet milling the suspension to achieve submicron particles of the labile agent; and c) removing the polymer solvent thereby forming a solid polymer matrix having the labile agent dispersed therein.

5. A method for preparing a composition for the sustained release of a labile agent, comprising the steps of:

a) forming a suspension comprising the labile agent wherein the labile agent is a protein, polypeptide or oligonucleotide dispersed in a polymer solution comprising at least one biocompatible polymer and at least one polymer solvent;

b) wet milling the suspension to achieve submicron particles of the labile agent;

c) adding a metal cation component to the suspension which modulates the release of the labile agent; and d) removing the polymer solvent thereby forming a solid polymer matrix having the labile agent dispersed therein.

6. The method of claim 4, wherein the metal component is selected from the group consisting of $Mg(OH)_2$, $MgCO_3$, $CaCO_3$, $ZnCO_3$, $Mg(OAc)_2$, $Zn(OAc)_2$, $ZnSO_4$, $MgCl_2$, $ZnCl_2$, $MgSO_4$, zinc citrate and magnesium citrate.

7. A method for preparing submicron particles of a labile agent, wherein said method comprises the steps of:

a) forming a suspension comprising the labile agent wherein the labile agent is a protein, polypeptide or oligonucleotide dispersed in a polymer solution comprising a poly(lactide-co-glycolide) polymer and at least one polymer solvent; and b) wet milling the suspension.

8. A method for preparing submicron particles of a labile agent, wherein said method comprises the steps of:

a) forming a suspension comprising the labile agent wherein the labile agent is a protein, polypeptide or oligonucleotide dispersed in a polymer solution comprising at least one biocompatible polymer and a polymer solvent selected from the group consisting of methylene chloride, acetone, ethyl acetate, methyl acetate, chloroform, dimethylsulfoxide, hexafluoroisopropanol and any combination thereof; and b) wet milling the suspension.

9. A method for preparing submicron particles of a labile agent, wherein said method comprises the steps of:

a) forming a suspension comprising human growth hormone complexed to a stabilizing metal cation and dispersed in a polymer solution comprising at least one biocompatible polymer and at least one polymer solvent; and b) wet milling the suspension.

10. The method of claim 9, wherein the human growth hormone is complexed to $Zn^{+2}$.

11. The method of claim 1 wherein the submicron particles have a volume median particle size of less than 1 micron, measured by laser diffraction.

12. The method of claim 1 wherein step (b) is conducted at a temperature of less than about 30° C.

13. The method of claim 12 wherein the temperature is less than about 10° C.

14. The method of claim 12 wherein the temperature is less than about 4° C.

15. The method of claim 1 wherein the labile agent is present in the suspension at a concentration of from about 0.01 to about 50% w/w of the combined weight of polymer and labile agent.

16. The method of claim 15 wherein the labile agent is present at a concentration of about 0.01 to 30% w/w of the combined weight of the polymer and labile agent.

17. The method of claim 1 wherein the biocompatible polymer is biodegradable.

18. The method of claim 17 wherein the biodegradable polymer is selected form the group consisting of poly (lactide)s, poly(glycolide)s, poly(lactide-coglycolide)s, poly (lactic acid)s, poly(glycolic acid)s, poly(lactic acid-co-glycolic acid)s, poly(caprolactone), polycarbonates, polyesteramides, polyanhydrides, poly(amino acid)s, poly (ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof.

19. The method of claim 1 wherein wet milling comprises the steps of:

a) adding a grinding media to the suspension; and b) applying a mechanical means.

20. The method of claim 19 wherein the mechanical means is a dispersion mill or rotary blender.

21. The method of claim 20 wherein the dispersion mill is selected from the group consisting of: a rotary mill, a ball mill, an attrition mill, a vibratory mill, a planetary mill, a media mill or a bead mill.

22. The method of claim 1 wherein the polymer solvent is selected from the group consisting of: methylene chloride, acetone, ethyl acetate, methyl acetate, chloroform, dimethylsulfoxide, hexafluoroisopropanol or a combination thereof.

23. The method of claim 3 wherein the submicron particles have a volume median particle size of less than 1 micron, measured by laser diffraction.

24. The method of claim 3 wherein step (b) is conducted at a temperature of less than about 30° C.

25. The method of claim 24 wherein the temperature is less than about 10° C.

26. The method of claim 24 wherein the temperature is less than about 4° C.

27. The method of claim 3 wherein the labile agent is present in the suspension at a concentration of from about 0.01 to about 50% w/w of the combined weight of polymer and labile agent.

28. The method of claim 27 wherein the labile agent is present at a concentration of about 0.01 to 30% w/w of the combined weight of the polymer and labile agent.

29. The method of claim 3 wherein the labile agent is a protein.

30. The method of claim 29 wherein the protein is complexed to a stabilizing metal cation.

31. The method of claim 30 wherein said stabilizing metal cation is selected from the group consisting of $Zn^{+2}$, $Ca^{+2}$, $Cu^{+2}$, $Mg^{+2}$, $K^+$ and any combination thereof.

32. The method of claim 31 wherein said stabilizing metal cation is $Zn^{+2}$.

33. The method of claim 3 wherein wet milling comprises the steps of:

a) adding a grinding media to the suspension; and b) applying a mechanical means.

34. The method of claim 33 wherein the mechanical means is a dispersion mill or rotary blender.

35. The method of claim 34 wherein the dispersion mill is selected from the group consisting of: a rotary mill, a ball mill, an attrition mill, a vibratory mill, a planetary mill, a media mill or a bead mill.

36. The method of claim 3 wherein the polymer solvent is selected from the group consisting of: methylene chloride, acetone, ethyl acetate, methyl acetate, chloroform, dimethylsulfoxide, hexafluoroisopropanol or a combination thereof.

37. The method of claim 4 wherein the submicron particles have a volume median particle size of less than 1 micron, measured by laser diffraction.

38. The method of claim 4 wherein step (b) is conducted at a temperature of less than about 30° C.

39. The method of claim 38 wherein the temperature is less than about 10° C.

40. The method of claim 38 wherein the temperature is less than about 4° C.

41. The method of claim 4 wherein the labile agent is present in the suspension at a concentration of from about 0.01 to about 50% w/w of the combined weight of polymer and labile agent.

42. The method of claim 41 wherein the labile agent is present at a concentration of about 0.01 to 30% w/w of the combined weight of the polymer and labile agent.

43. The method of claim 4 wherein the labile agent is a protein.

44. The method of claim 43 wherein the protein is complexed to a stabilizing metal cation.

45. The method of claim 44 wherein said stabilizing metal cation is selected from the group consisting of $Zn^{+2}$, $Ca^{+2}$, $Cu^{+2}$, $Mg^{+2}$, $K^+$ and any combination thereof.

46. The method of claim 45 wherein said stabilizing metal cation is $Zn^{+2}$.

47. The method of claim 4 wherein the biocompatible polymer is biodegradable.

48. The method of claim 47 wherein the biodegradable polymer is selected form the group consisting of poly (lactide)s, poly(glycolide)s, poly(lactide-coglycolide)s, poly (lactic acid)s, poly(glycolic acid)s, poly(lactic acid-coglycolic acid)s, poly(caprolactone), polycarbonates, polyesteramides, polyanhydrides, poly(amino acid)s, poly (ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof.

49. The method of claim 4 wherein wet milling comprises the steps of:
   a) adding a grinding media to the suspension; and
   b) applying a mechanical means.

50. The method of claim 49 wherein the mechanical means is a dispersion mill or rotary blender.

51. The method of claim 50 wherein the dispersion mill is selected from the group consisting of: a rotary mill, a ball mill, an attrition mill, a vibratory mill, a planetary mill, a media mill or a bead mill.

52. The method of claim 5 wherein the submicron particles have a volume median particle size of less than 1 micron, measured by laser diffraction.

53. The method of claim 5 wherein step (b) is conducted at a temperature of less than about 30° C.

54. The method of claim 53 wherein the temperature is less than about 10° C.

55. The method of claim 53 wherein the temperature is less than about 4° C.

56. The method of claim 5 wherein the labile agent is present in the suspension at a concentration of from about 0.01 to about 50% w/w of the combined weight of polymer and labile agent.

57. The method of claim 56 wherein the labile agent is present at a concentration of about 0.01 to 30% w/w of the combined weight of the polymer and labile agent.

58. The method of claim 5 wherein the labile agent is a protein.

59. The method of claim 58 wherein the protein is complexed to a stabilizing metal cation.

60. The method of claim 59 wherein said stabilizing metal cation is selected from the group consisting of $Zn^{+2}$, $Ca^{+2}$, $Cu^{+2}$, $Mg^{+2}$, $K^+$ and any combination thereof.

61. The method of claim 60 wherein said stabilizing metal cation is $Zn^{+2}$.

62. The method of claim 5 wherein the biocompatible polymer is biodegradable.

63. The method of claim 62 wherein the biodegradable polymer is selected form the group consisting of poly (lactide)s, poly(glycolide)s, poly(lactide-coglycolide)s, poly (lactic acid)s, poly(glycolic acid)s, poly(lactic acid-coglycolic acid)s, poly(caprolactone), polycarbonates, polyesteramides, polyanhydrides, poly(amino acid)s, poly (ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof.

64. The method of claim 5 wherein wet milling comprises the steps of:
   a) adding a grinding media to the suspension; and
   b) applying a mechanical means.

65. The method of claim 64 wherein the mechanical means is a dispersion mill or rotary blender.

66. The method of claim 65 wherein the dispersion mill is selected from the group consisting of: a rotary mill, a ball mill, an attrition mill, a vibratory mill, a planetary mill, a media mill or a bead mill.

67. The method of claim 5 wherein the polymer solvent is selected from the group consisting of: methylene chloride, acetone, ethyl acetate, methyl acetate, chloroform, dimethylsulfoxide, hexafluoroisopropanol or a combination thereof.

68. The method of claim 7 wherein the submicron particles have a volume median particle size of less than 1 micron, measured by laser diffraction.

69. The method of claim 7 wherein step (b) is conducted at a temperature of less than about 30° C.

70. The method of claim 69 wherein the temperature is less than about 10° C.

71. The method of claim 69 wherein the temperature is less than about 4° C.

72. The method of claim 7 wherein the labile agent is present in the suspension at a concentration of from about 0.01 to about 50% w/w of the combined weight of polymer and labile agent.

73. The method of claim 72 wherein the labile agent is present at a concentration of about 0.01 to 30% w/w of the combined weight of the polymer and labile agent.

74. The method of claim 7 wherein the labile agent is a protein.

75. The method of claim 74 wherein the protein is complexed to a stabilizing metal cation.

76. The method of claim 75 wherein said stabilizing metal cation is selected from the group consisting of $Zn^{+2}$, $Ca^{+2}$, $Cu^{+2}$, $Mg^{+2}$, $K^+$ and any combination thereof.

77. The method of claim 76 wherein said stabilizing metal cation is $Zn^{+2}$.

78. The method of claim 7 herein wet milling comprises the steps of:
   a) adding a grinding media to the suspension; and
   b) applying a mechanical means.

79. The method of claim 78 wherein the mechanical means is a dispersion mill or rotary blender.

80. The method of claim 79 wherein the dispersion mill is selected from the group consisting of: a rotary mill, a ball mill, an attrition mill, a vibratory mill, a planetary mill, a media mill or a bead mill.

81. The method of claim 7 wherein the polymer solvent is selected from the group consisting of: methylene chloride, acetone, ethyl acetate, methyl acetate, chloroform, dimethylsulfoxide, hexafluoroisopropanol or a combination thereof.

82. The method of claim 8 wherein the submicron particles have a volume median particle size of less than 1 micron, measured by laser diffraction.

83. The method of claim 8 wherein step (b) is conducted at a temperature of less than about 30° C.

84. The method of claim 83 wherein the temperature is less than about 10° C.

85. The method of claim 83 wherein the temperature is less than about 4° C.

86. The method of claim 83 wherein the labile agent is present in the suspension at a concentration of from about 0.01 to about 50% w/w of the combined weight of polymer and labile agent.

87. The method of claim 86 wherein the labile agent is present at a concentration of about 0.01 to 30% w/w of the combined weight of the polymer and labile agent.

88. The method of claim 7 wherein the labile agent is a protein.

89. The method of claim 88 wherein the protein is complexed to a stabilizing metal cation.

90. The method of claim 89 wherein said stabilizing metal cation is selected from the group consisting of $Zn^{+2}$, $Ca^{+2}$, $Cu^{+2}$, $Mg^{+2}$, $K^+$ and any combination thereof.

91. The method of claim 90 wherein said stabilizing metal cation is $Zn^{+2}$.

92. The method of claim 8 wherein the biocompatible polymer is biodegradable.

93. The method of claim 92 wherein the biodegradable polymer is selected form the group consisting of poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof.

94. The method of claim 8 wherein wet milling comprises the steps of:
   a) adding a grinding media to the suspension; and
   b) applying a mechanical means.

95. The method of claim 94 wherein the mechanical means is a dispersion mill or rotary blender.

96. The method of claim 95 wherein the dispersion mill is selected from the group consisting of: a rotary mill, a ball mill, an attrition mill, a vibratory mill, a planetary mill, a media mill or a bead mill.

97. The method of claim 9 wherein the submicron particles have a volume median particle size of less than 1 micro, measured by laser diffraction.

98. The method of claim 9 wherein step (b) is conducted at a temperature of less than about 30° C.

99. The method of claim 98 wherein the temperature is less than about 10° C.

100. The method of claim 98 wherein the temperature is less than about 4° C.

101. The method of claim 9 wherein the labile agent is present in the suspension at a concentration of from about 0.04 to about 50% w/w of the combined weight of polymer and labile agent.

102. The method of claim 101 wherein the labile agent is present at a concentration of about 0.01 to 30% w/w of the combined weight of the polymer and labile agent.

103. The method of claim 9 wherein the biocompatible polymer is biodegradable.

104. The method of claim 103 wherein the biodegradable polymer is selected form the group consisting of poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof.

105. The method of claim 9 wherein wet milling comprises the steps of:
   a) adding a grinding media to the suspension; and
   b) applying a mechanical means.

106. The method of claim 105 wherein the mechanical means is a dispersion mill or rotary blender.

107. The method of claim 106 wherein the dispersion mill is selected from the group consisting of: a rotary mill, a ball mill, an attrition mill, a vibratory mill, a planetary mill, a media mill or a bead mill.

108. The method of claim 9 wherein the polymer solvent is methylene chloride, acetone, ethyl acetate, methyl acetate, chloroform, dimethylsulfoxide, hexafluoroisopropanol and a combination thereof.

* * * * *

UNITED STATES PATENT AND TRADEMARK OFFICE
CERTIFICATE OF CORRECTION

PATENT NO.     : 6,444,223 B1
DATED          : September 3, 2002
INVENTOR(S)    : Mark A. Tracy, Kevin L. Ward and Warren E. Jaworowicz It is certified that error appears in the above-identified patent and that said Letters Patent is hereby corrected as shown below:

Column 15,
Line 29, delete "claim 4", insert -- claim 5 --.

Column 16,
Line 14, delete "form", insert -- from --.

Column 17,
Line 41, delete "form", insert -- from --.

Column 18,
Line 21, delete "form", insert -- from --.

Column 19,
Line 3, delete "herein", insert -- wherein --;
Line 27, delete "claim 83", insert -- claim 8 --;
Line 46, delete "form", insert -- from --.

Column 20,
Line 22, delete "0.04", insert -- 0.01 --;
Line 30, delete "form", insert -- from --.

Signed and Sealed this

Seventh Day of January, 2003

JAMES E. ROGAN
*Director of the United States Patent and Trademark Office*